(12) United States Patent
Beaty et al.

(10) Patent No.: US 12,031,118 B2
(45) Date of Patent: Jul. 9, 2024

(54) REACTANCE AND CAPACITANCE SENSING PLATFORM FOR DETECTING MICROORGANISMS

(71) Applicant: BECTON DICKINSON AND COMPANY, Franklin Lakes, NJ (US)

(72) Inventors: Patrick Shawn Beaty, Dallastown, PA (US); Michael A. Brasch, Gaithersburg, MD (US); Suneil Hosmane, Franklin Lakes, NJ (US); David Polley, Cockeysville, MD (US); Julie L Rosales, Randallstown, MD (US); Kerry Lynn Smith, York, PA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 433 days.

(21) Appl. No.: 17/019,802

(22) Filed: Sep. 14, 2020

(65) Prior Publication Data
US 2020/0407677 A1    Dec. 31, 2020

Related U.S. Application Data

(62) Division of application No. 15/518,989, filed as application No. PCT/US2015/055501 on Oct. 14, 2015, now Pat. No. 10,808,217.
(Continued)

(51) Int. Cl.
 *C12M 1/34* (2006.01)
 *C12Q 1/02* (2006.01)
 (Continued)

(52) U.S. Cl.
 CPC .............. *C12M 41/36* (2013.01); *C12Q 1/02* (2013.01); *C12Q 1/04* (2013.01); *G01N 27/02* (2013.01);
(Continued)

(58) Field of Classification Search
None
See application file for complete search history.

(56) References Cited

U.S. PATENT DOCUMENTS

| 6,433,560 B1 | 8/2002 | Hansen et al. |
| 10,094,818 B2 | 10/2018 | Connolly et al. |

(Continued)

FOREIGN PATENT DOCUMENTS

| CN | 1256756 A | 6/2000 |
| CN | 101698879 A | 4/2010 |

(Continued)

OTHER PUBLICATIONS

Sengupta et al., "A micro-scale multi-frequency reactance measurement technique to detect bacterial growth at low bio-particle concentrations," Lap Chip, vol. 6, pp. 683-692 (2006) (Year: 2006).*

(Continued)

*Primary Examiner* — Matthew D Krcha
(74) *Attorney, Agent, or Firm* — Botos Churchill IP Law LLP (57) ABSTRACT

A system and method with increased sensitivity to microorganism growth. The system includes signal processing electronic circuit connected to a consumable or vessel through two or more electrodes that fully penetrate the vessel and are in contact with the fluid contents. The electronic circuit is configured to detect a component of the total impedance of the sample, specifically the "out-of-phase" or imaginary reactance component, which has a sensitive response to organism growth in a frequency-dependent manner. The system detects changes in both the composition of charged molecules in the liquid matrix and the number of microorganisms based on monitoring the sample for change in this parameter. This results in a 5-70% reduction in time-to-detection (TTD).

(Continued)

The system and method detect organisms in a plurality of vessel shapes, volumes, and matrix (or media) formats. The electrodes are fully immersed in a continuous body of liquid sample. The distance between electrodes may be adjusted or tuned to fit the needs of the vessel. The voltage inputs can also be adjusted to allow proper detection of the contents within the vessel.

14 Claims, 10 Drawing Sheets

Related U.S. Application Data (60) Provisional application No. 62/063,602, filed on Oct. 14, 2014.

(51) Int. Cl.
  *C12Q 1/04* (2006.01)
  *G01N 27/02* (2006.01)
  *G01N 33/487* (2006.01)
  *G01N 33/49* (2006.01)

(52) U.S. Cl.
  CPC ..... *G01N 33/48785* (2013.01); *G01N 27/026* (2013.01); *G01N 33/49* (2013.01)

(56) References Cited

U.S. PATENT DOCUMENTS

| | | | |
|---|---|---|---|
| 2002/0197709 | A1 | 12/2002 | Van der Weide et al. |
| 2007/0090927 | A1 | 4/2007 | Potyrailo et al. |
| 2007/0238092 | A1* | 10/2007 | Rubesa ............... G01N 37/005 435/287.1 |
| 2009/0098645 | A1 | 4/2009 | Fang et al. |
| 2011/0144469 | A1 | 6/2011 | Connolly et al. |
| 2017/0240855 | A1 | 8/2017 | Beaty et al. |
| 2020/0011847 | A1* | 1/2020 | Bruckmann ..... G01N 35/00732 |

FOREIGN PATENT DOCUMENTS

| | | |
|---|---|---|
| CN | 102016575 A | 4/2011 |
| CN | 102954985 A | 3/2013 |
| CN | 104380090 A | 2/2015 |
| CN | 205538786 U | 8/2016 |
| EP | 1162449 A1 | 12/2001 |
| TW | 201226896 A | 7/2012 |
| WO | 9942847 A1 | 8/1999 |
| WO | 0022431 A1 | 4/2000 |
| WO | 2013123189 A1 | 8/2013 |

OTHER PUBLICATIONS

"The Wien Bridge Oscillator," http://www.play-hookey.com/oscillators/audio/wien_bridge_oscillator.html, obtained using Wayback Machine from Jan. 20, 2013 (Year: 2013).*

EP Article 94 Communication issued in EP application No. 158532218 on Jun. 14, 2021., pp. 7.

Goncalves, J. J., et al., ""Rapid Evaluation of biofilm attachment promoters and biofilm growth orientation using a mini-impedimetric device"", Sensors and Actuators B: Chemical, Elsevier BV, NL, vol. 143 No. 1, XP026754260, ISSN: 0925-4005, DOI: 10.1016/J.SNB.2009.07.036 [retrieved on Jul. 30, 2007], Dec. 4, 2009, pp. 341-348.

"The Wien Bridge Oscillator," http://www.play-hookey.com/oscillators/audio/wien_bridge_oscillator.html, obtained using Wayback Machine from Jan. 20, 2013, hereinafter Wien Bridge. (Year: 2013).

Chinese First Office Action issued in corresponding CN application No. 2015-800551755 dated Feb. 1, 2019.

Chinese Office Action issued in corresponding CN application No. 201580055175.5 dated Sep. 26, 2019.

First Examination Report issued in corresponding Australian Application No. 2015336363 dated Apr. 22, 2020.

International Search Report and Written Opinion for Application No. PCT/US2015/055501 dated Jan. 25, 2016.

Japanese Office Action issued in JP application No. 2017518797 dated Nov. 22, 2019.

Sengupta el. al., "A micro-scale multi-frequency reactance measurement technique to detect bacterial growth at low bio-particle concentrations," Lab Chip, vol. 6, pp. 682-692 (2006).

Third Office Action issued in corresponding Chinese Application No. 2015800551755 dated Apr. 13, 2020.

Search Report received in EP15853221.8 dated Mar. 29, 2018, pp. 6.

Varshney, M. et al., Double Interdigitated Array Microelectrode-Based Impedance Biosensor for Detection of Viable *Escherichia coli* O157:H7 in Growth Medium, Talanta, 2008, vol. 74, , (2008), pp. 518-525.

Kim, YH. et al., An impedimetric biosensor for real-time monitoring of bacterial growth in a microbial fermentor, Sensors and Actuators. B. Chemical. vol. 138,, (2009), pp. 270-277.

Masaaki Kobayashi et al., Real-time monitoring of cell growth rate by means of electrochemical impedance measurement, The 48th Jidouseigyorengo Conference, C2-16, (Jan. 1, 2006), pp. 513-516.

Ramirez, Nardo , et al., ""Electrical Impedance Spectroscopy as a Powerful Analytical Tool for Monitoring Microbiological Growth on Medical Implants","", Encyclopedia of Healthcare Information Systems, Feb. 1, 2009 XP055463735, ISBN: 978-1-59904-889-5 Retrieved from the Internet: URL:https://pdfs.semanticscholar.org/6455/aaccleb487042dla5e332e0c635c54377414.pdf [retrieved on Mar. 28, 2018], (Feb. 1, 2009), pp. 7.

Sengupta Shramik, et al., "A micro-scale multi-frequency reactance measurement technique to detect", Lab Chip. 2006, 6, 682-692.

Zhang, Aiping , et al., "Rapid Detection of Total Bacteria Count in Milk by the Impedance Method, Journal of Chinese Institute of Food Science and Technology", vol. 12 No. 2, (Feb. 2012), pp. 158-164.

Decision of Final Rejection for Chinese Patent Application No. 2015800551755 dated Nov. 4, 2020.

Full Examination Report issued in Australian Application No. 2015336363 dated Dec. 17, 2020.

Office Action issued in corresponding Chinese Patent Application No. 201580055175.5 dated Jul. 15, 2022, (28 pp.).

Office Action issued in corresponding European Patent Application No. 15853221.8 dated May 25, 2023 (8 pp.).

Yang, et al, Detection of Viable *Salmonella typhimurium* by Impedance Measurement of Electrode Capacitance and Medium Resistance, Biosensors & Bioelectronics, Jun. 30, 2003, pp. 495-502.

Chinese First Office Action issued in corresponding CN application No. 2022116971984 dated Jun. 27, 2023, pp. 12.

Chinese Office Action issued in corresponding CN application No. 2022116971984 on Feb. 29, 2024., pp. 13.

* cited by examiner

| MEDIA (mL) | BLOOD (mL) | ORGANISM | EST. TTD (Hrs) | HISTORIC BACTEC TTD (Hrs) | % FASTER |
|---|---|---|---|---|---|
| STANDARD AEROBIC (11) | BAGGED (3) | A25922-E. COLI | 9 | 10-11 | 14% |
| STANDARD AEROBIC (11) | BAGGED (3) | A25923-S. AUREUS | 7-8 | 12-14 | 42% |
| MYCOLYTIC ML1D (7) | BAGGED (7) | A25922-E. COLI | 8.5-9 | 10-11 | 14% |
| MYCOLYTIC ML1D (7) | BAGGED (7) | A25923-S. AUREUS | 10 | 12-14 | 23% |
| MYCOLYTIC ML1D (7) | BAGGED (7) | A19418-H. INFLUENZAE | 16 | 17-21 | 16% |
| MYCOLYTIC ML1D (7) | BAGGED (7) | A29212-E. FAECALIS | 11 | 11-12 | 8% |
| MYCOLYTIC ML1D (7) | BAGGED (7) | A66032-C. GLABRATA | 17 | 20-42 | 45% |

REACTANCE AND CAPACITANCE SENSING PLATFORM FOR DETECTING MICROORGANISMS

CROSS-REFERENCE TO RELATED APPLICATIONS

The present application is a divisional of U.S. application Ser. No. 15/518,989, filed Apr. 13, 2017, now U.S. Pat. No. 10,808,217, issued Oct. 20, 2020, which application is a national phase entry under 35 U.S.C. § 371 of International Application No. PCT/US2015/055501 filed Oct. 14, 2015, published in English, which claims priority from U.S. Provisional Application No. 62/063,602, filed Oct. 14, 2014, all of which are incorporated herein by reference.

BACKGROUND OF THE INVENTION

The present invention relates to the field of microbial detection in clinical samples. The invention is in particular related to achieving faster detection of the presence or absence of bacteria in a biological sample.

The ability to detect replicating microorganisms (bacteria, fungi, viruses) is a fundamental requirement within many clinical microbiological applications. In this regard, several direct and/or indirect methods for detecting organism growth have been developed.

For example, indirect detection methods may estimate the effects of by-products, molecules, compounds, or chemical reactants on organism growth/replication. That is, whether the by-products, molecules, compounds, or chemical reactants collectively and cumulatively increase, decrease, or become altered as a result of organism growth/replication. For instance, the changing metabolic demands of a growing microorganism population may be observed through a change in fluorescence or through a colorimetric change of an elastomeric sensor. While such detection mechanisms are well-known, the detection threshold is exceeded when organism concentrations reach approximately $10^9$ colony forming units (CFU) per bottle. This results in typical time-to-detection (TTD) in the range of 8 to 24 hours for many clinically relevant blood stream pathogens. In some cases, certain organisms may require more than 72 hours for detection.

Additionally, electrical detection systems have been developed to detect viable microorganisms in solution. In general, these platforms utilize impedance measurements as an indirect indicator of microorganism growth. One such system is described in WO 2013/123189 filed on Feb. 14, 2013 and entitled "Impendence-Based Bacterial Detection System" which is commonly assigned with the present application and hereby incorporated by reference.

Through the excretion or uptake of charged products (e.g. ions, phosphates, sulfates, nitrates) or production of charged metabolic intermediates (e.g., lactic acid), the total ionic makeup of the sample is altered when microbial growth occurs. Microbial growth affects the overall conductivity (or resistivity) of the medium. This change in conduction (or resistance) manifests itself by changes in the overall electrical impedance of the solution over time. Impedance is measured by immersing a plurality of electrodes into the solution and measuring either the voltage (e.g., AC or DC) and/or current response. These systems typically use data modeling to fit a theoretical framework around raw impedance data to extract information pertaining to microorganism growth.

For example, some well-known systems use a 10 mL reaction cell filled with a specialized broth. The reaction cell is inoculated with industrial microbiological samples and incubated for up to 24 hrs. A fixed frequency (10 kHz) input waveform is supplied into the tube and the impedance is monitored. As the ionic composition of the medium changes in response to microbial growth over time, small changes in media conduction begin to accumulate. When the conductivity has increased above a specified threshold, an indication of a sample testing positive for microbial growth is returned. However, systems of these types have major technical limitations such that the scope of their application has been limited mainly to industrial microbiological applications.

In this regard, electrical detection systems suffer from a technical limitation in that they rely on a conduction or resistance change in the growth medium due to formation and accumulation of by-products of microbial growth. Consequently, for high-ionic strength mediums, any signal generated by microbial replication is essentially masked until a very high concentration of microorganisms is present. Additionally, many applications that monitor a highly complex medium (e.g., blood) for microorganism growth and detection cannot use standard impedance based detection techniques.

One proposed solution to the problems with impedance detection systems suggests using a subset of the total impedance to increase sensitivity to measurements indicative of microorganism growth. In Sengupta et. al., "A micro-scale multi-frequency reactance measurement technique to detect bacterial growth at low bio-particle concentrations," Lab Chip, Vol. 6, pp. 682-692 (2006) (hereinafter "Sengupta"), a microfluidic chamber of 100 µL volume was used as a chamber that was monitored for a response that would indicate the presence of bacteria. Sengupta et. al. reports that the sensing response can be improved relative to a simple dielectric conductivity measurement by providing a long (cm scale) and very thin (<250 microns) channel-like chamber containing the sample, with very small electrodes positioned at both ends. By using very high frequencies (from 100 kHz to 100 MHz), the capacitance contribution of the liquid sample was measured. According to Sengupta, the capacitance in the liquid sample is sensitive to changes caused by the presence and/or growth of bacteria in the sample disposed in the chamber.

However, Sengupta states that temperature fluctuations were the most significant challenge to the use of the method of using a microfluidic environment to assay for the presence of bacteria in a sample using a dielectric conductivity measurement. Additionally, Sengupta obtains and measures a new sample for each analytical time point. That is, Sengupta requires filling a new microfluidics chamber (or replacing the liquid sample in the microfluidics chamber with fresh sample) before making a subsequent measurement. This approach is destructive as it requires consumption of approximately 100-200 µL of sample per hour, as each previously sampled portion is discarded. The volume of sample consumption over time could present a serious challenge, especially for samples with slow growing or slow metabolism microorganisms. Additionally, obtaining samples over time has inherent biohazard waste disposal and sterility concerns.

Another disadvantage of the technique described in Sengupta is the need to perform the experiment on the microliter volume scale. This prohibits the technique from sensing clinically relevant samples without the proper preparation or sub-sampling steps. Furthermore, the technique utilizes raw spectrum data from a wide range of frequencies (hundreds to thousands of kHz) to computationally fit to a circuit model of the "capacitance" of the solution. Thus, there is mathematical complexity surrounding the analysis of the data, which may result in up to a minute of post-processing time per consumable.

Finally, Sengupta does not overcome the inherent incompatibility of high ionic media (e.g., blood) with the described impedance technique. Instead, Sengupta circumvents the problem by limiting the total number of ions by reducing the overall volume of the detection chamber. Therefore, even slightly higher volumes result in a large loss in sensitivity.

Therefore, there exists a need for improvement in the use of dielectric measurements to detect the presence or absence of microbes in a liquid.

BRIEF SUMMARY OF THE INVENTION

The present application describes an impedance-based method and system that uses a sub-component, i.e. the imaginary (reactance) component, of the total impedance to determine the total ionic composition of the medium. In this regard, the reactance sub-component has much higher sensitivity to both the change in ionic components of the media due to microorganism growth (indirect detection) and the charged cellular mass of the microorganisms (direct detection). This provides a broad detection approach for dealing with a wide and diverse spectrum of microorganisms.

The current application also describes a tuning method to allow reactance detection within fluid volumes that span from the microliter to milliliter ranges. In this regard, in one embodiment, the frequency sensitivity of the system may be changed from 1 kHz to hundreds of kHz by tuning the physical value of resistors in parallel to a capacitive input stage of a lock-in amplifier detector. This results in an increased sensitivity towards changes in ionic composition (for operating frequencies between 1-20 kHz) and microbial biomass (for operation frequencies much greater than 20 kHz).

According to an alternative implementation, the current application describes a method for tuning the frequency sensitivity of the target sample through the use of a bridge resistor-capacitor tuning circuit. By tuning the values of the bridge resistor-capacitor tuning circuit, the detection becomes sensitive to both changes in ionic composition and the charged organism mass in the high frequency spectrum (>>20 kHz). Thus, the bridge resistor-capacitor tuning circuit yields faster time-to-detections (TTDs).

Furthermore, tuning the frequency response within the test consumable allows for the detection of microbial growth in relatively large volumes (e.g. >10 mL) of sample. This eliminates the prior art need to constantly sub-sample. Additional benefits are realized by utilizing the raw reactance data since complex mathematical calculations may no longer be required after each sample. The reduced computational complexity coupled to the utilization of a narrower range of frequencies allows for faster scan times (milliseconds to seconds versus seconds to minutes).

The current application also describes a system with increased sensitivity to microorganism growth. The system includes signal processing electronic circuit connected to a test cell (i.e., consumable) through two or more electrodes that fully penetrate the test cell and are in contact with the fluid contents. The electronic circuit is configured to detect a component of the total impedance, specifically the "out-of-phase" or imaginary reactance component, which has a sensitive response to organism growth in a frequency-dependent manner. The reactance component of impedance is well-known to one skilled in the art and is not described in detail herein. In this regard, the system may detect changes in both the composition of charged molecules in the liquid matrix and the number of microorganisms based on monitoring the sample for change in this parameter. This results in a 5-70% reduction in time-to-detection (TTD).

Another advantage realized by the system and method described herein is the ability to detect organisms in a plurality of consumable shapes, volumes, and matrix (or media) formats. In this regard, the electrodes should be fully immersed in a continuous body of liquid sample. The distance between electrodes may be adjusted or tuned to fit the needs of the consumable. Furthermore, the voltage inputs can also be adjusted to allow proper detection of the contents within the consumable.

In this regard, the current system is capable of sensing microorganisms present in what would otherwise be deemed "dirty" samples due to the highly charged nature of microorganism cell walls and their respective changes in the ionic composition of the liquid matrix. That is, the current system may monitor growth in an antimicrobial susceptibility test situation with blood contaminants and other constituents of the sample that would otherwise disrupt optical detection strategies.

DETAILED DESCRIPTION

According the examples described herein, the presence or absence of microbial growth is determined using an impedance sub-component measurement. The electrode configuration and the frequency may be configured as described herein to ensure that even small changes in the ionic charge of the test environment are detectable to determine the presence or absence of microbial growth.

Impedance is a measurement of the electrical opposition that a circuit presents to a current when a voltage is applied. When operating in an alternating current (AC, f>0) circuit, impedance is composed of resistance and reactance. In contrast, impedance is only composed of resistance in a direct current (DC, f=0) circuit. Thus, impedance may be expressed as:

$$Z=Zo+j*Zr(f)$$

where Z=impedance, Zo=Resistance, j=√−1, Zr=Reactance, and f=frequency. Thus, impedance is an electrical characteristic of a substance that is comprised of two sub-components, resistance and reactance.

Resistance is the opposition to the passage of an electrical current through an electrical conductor (e.g., metal wire, salt water solution, etc.). Resistance is a scalar value and is not frequency dependent. Accordingly, resistance has an inverse relationship with the total number of static (non-evolving) charged species (i.e., ions, protons, amino acids, peptides, small molecules, etc.) that are contained within a given sample. An increase in charged species results in a lower resistance while, conversely, a decrease results in a higher resistance. During microbial replication (commonly referred to as microbial growth), the total number of charged particles will continue to change in an organism-dependent manner. For example, as new cells divide, ions are taken from the media and incorporated into the daughter cells. Thus, cell division results in a decreased number of charged species. At the same time, organisms metabolize nutrients in the medium and produce charged products that result in an increase in the number of charged species.

Reactance, on the other hand, is the opposition of a circuit element to a change of electric current or voltage, due to that element's inductance or capacitance. Reactance is similar to electrical resistance, but differs in that reactance is sensitive to operating frequency. Accordingly, reactance has an inverse relationship with the total number of capacitive components that are contained within a given sample. In this regard, capacitance within biological samples is manifested in two ways. First, charged species (typically molecules, non-microbial cells, etc.) accumulate at the site of the electrode interface due to the application of a sensing voltage (or potential). This is because charged molecules of an opposite polarity are attracted to the electrode when a voltage (e.g., positive or negative) is applied to an electrode in an attempt to neutralize the charge on the surface electrode. Another layer of molecules having the opposite charge form on those molecules to create a "coating effect" resulting in approximately no net charge at the electrode interface. This coating effect results in an electrical bi-layer or bi-layer capacitor (e.g., electric double-layer capacitor) having a neutral charge, like an insulator. Thus, the insulator-like coating causes a capacitive effect (i.e. an insulator flanked by the conducting medium and the electrode metal), referred to as interface capacitance.

Interface capacitance (Ci) is greatest when the system is operating at low frequencies (<15 kHz). With respect to detecting microbial growth, the interface capacitance changes when there are changes in ionic composition of the medium due to increases in microbial cell mass and associated metabolites. As such, interface capacitance is an indirect indicator of microorganism growth.

The other biological contributor to reactance is the capacitance of the cell. In this regard, human and non-human cells have charged outer cell membranes, followed by an insulating membrane core, and finally highly ionic inner cell components (e.g. ions). This is similar to the interface capacitance discussed above and shall be referred to as cellular capacitance or membrane capacitance (Cm).

In contrast to impedance, conductivity is a measurement related to the presence or absence of metabolic bacterial byproducts (e.g., gases, such as $CO_2$). In this regard, the capacitive components (and the changes in those components over time) discussed above more directly reflect the presence or absence of microorganisms (e.g., bacteria) in a sample container.

The method and system described herein detects interface capacitance (Ci) and/or cellular capacitance (Cm) as manifested by changes in electrical reactance through the use of an external frequency tuning circuit. This results in high detection sensitivity to both increases in organism biomass and changes in the sample environment induced by microorganism-related metabolic activity. The external frequency tuning circuit is compatible with a plurality of media volumes ranging from a microliter to more than a milliliter. Furthermore, the external frequency turning circuit allows for continuous monitoring without requiring periodic sub-sampling and refreshing of the sample being used.

Figure 1:
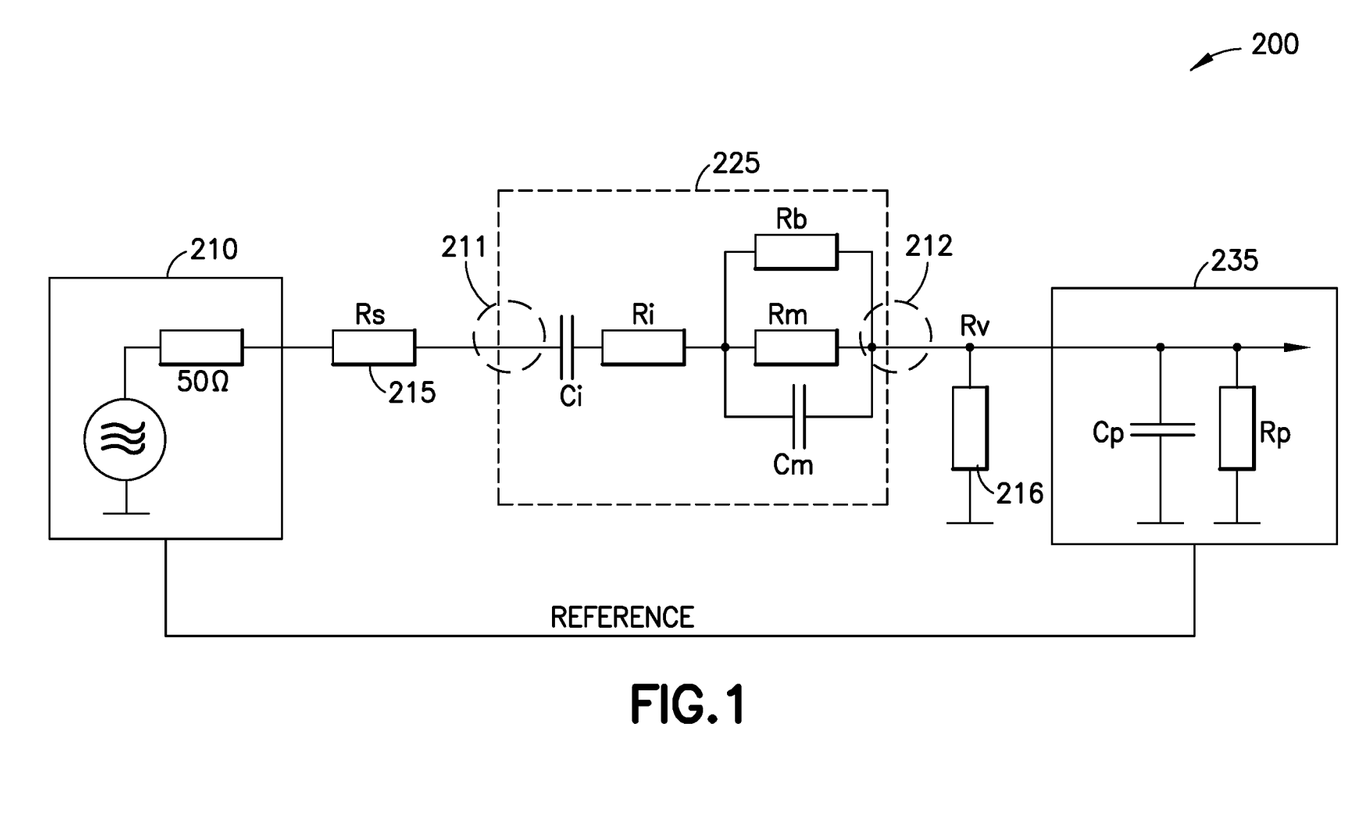
FIG. 1 illustrates an example of an apparatus for measuring the dielectric capacitance of a liquid sample to determine the presence or absence of microorganisms therein.

FIG. 1 is a detailed illustration showing an apparatus for detecting microbial growth based on a measurement of the capacitive impedance of the component. A lock-in amplifier is shown having an output stage 210 and an input stage 235. The output stage 210 includes an internal signal generator that may be used to feed a sinusoidal RF signal to one electrode 211 of a dielectric impedance measuring chamber 220 (not shown). The second electrode 212 of said chamber is connected with the signal input stage 235 of said lock-in amplifier. While a lock-in amplifier is shown in the figures and described in the examples herein, one of ordinary skill in the art would recognize that other measuring devices, such as an LCR meter or a network analyzer, may be used in place of the lock-in amplifier.

According to this implementation, the sample liquid within said chamber 220 (not shown) is in direct contact with the two electrodes and can be described by the circuit diagram shown in the dashed box 225. In this regard, Ci represents the interface capacitance between the metal electrodes and the liquid; Ri represents the interface resistance between the metal electrodes and the liquid; Rb is the bulk resistance of the liquid; Rm is the membrane resistance of the microorganisms; and Cm is the membrane capacitance.

It is assumed that internal signal generator in the output stage 210 of the lock-in amplifier has a typical internal resistance of 50Ω, and that the lock-in amplifier input stage 235 has a typical capacitance (Cp) of 15 pF and a typical input resistance (Rp) of 10 MΩ.

The apparatus for detecting microbial growth shown in FIG. 1 includes a source-matching resistor Rs (215) and a measuring load resistor Rv (216). According to FIG. 1, the source-matching resistor 215 and the measuring load resister 216 may be selected for a given dielectric measuring chamber and liquid, such that the frequency spectrum of the out-of-phase component of the measurement signal shows a zero-crossing feature that (i) is dependent on the value of Cm, and (ii) is set at a conveniently low frequency. In certain embodiments that frequency is set at a value at or below about 100 kHz. This allows for the use of standard lock-in amplifiers. For example when Rs=500Ω and Rv=500Ω, zero-crossing frequencies within the range of about 30 kHz to about 100 kHz are produced when the liquid sample medium is a conventional blood culture growth media. One example of such blood culture growth media is a Standard Aerobic/F media from Becton Dickinson Diagnostics in Sparks, MD.

According to FIG. 1, the out-of-phase signal amplitude with the output stage 210 of the lock-in amplifier is inversely proportional to the out-of-phase impedance value. In other words, the out-of phase impedance value (e.g., the reactance value) is at its maximum at a zero-crossing frequency of the out-of-phase signal amplitude as measured. It should be noted that changing the dimensions of the impedance measuring chamber (thereby altering the volume of the sample, the height/width ratio of the sample or both), or replacing the growth media with another liquid sample, will likely change the selected values for Rs and Rm. As illustrated, the lock-in amplifier input stage 235 provides reference potential. The reference as illustrated is a floating ground. One of ordinary skill will appreciate that there are many different ways to provide a reference potential by the input stage, and that the reference in FIG. 1 is merely illustrative and not by way of limitation.

Figure 2:
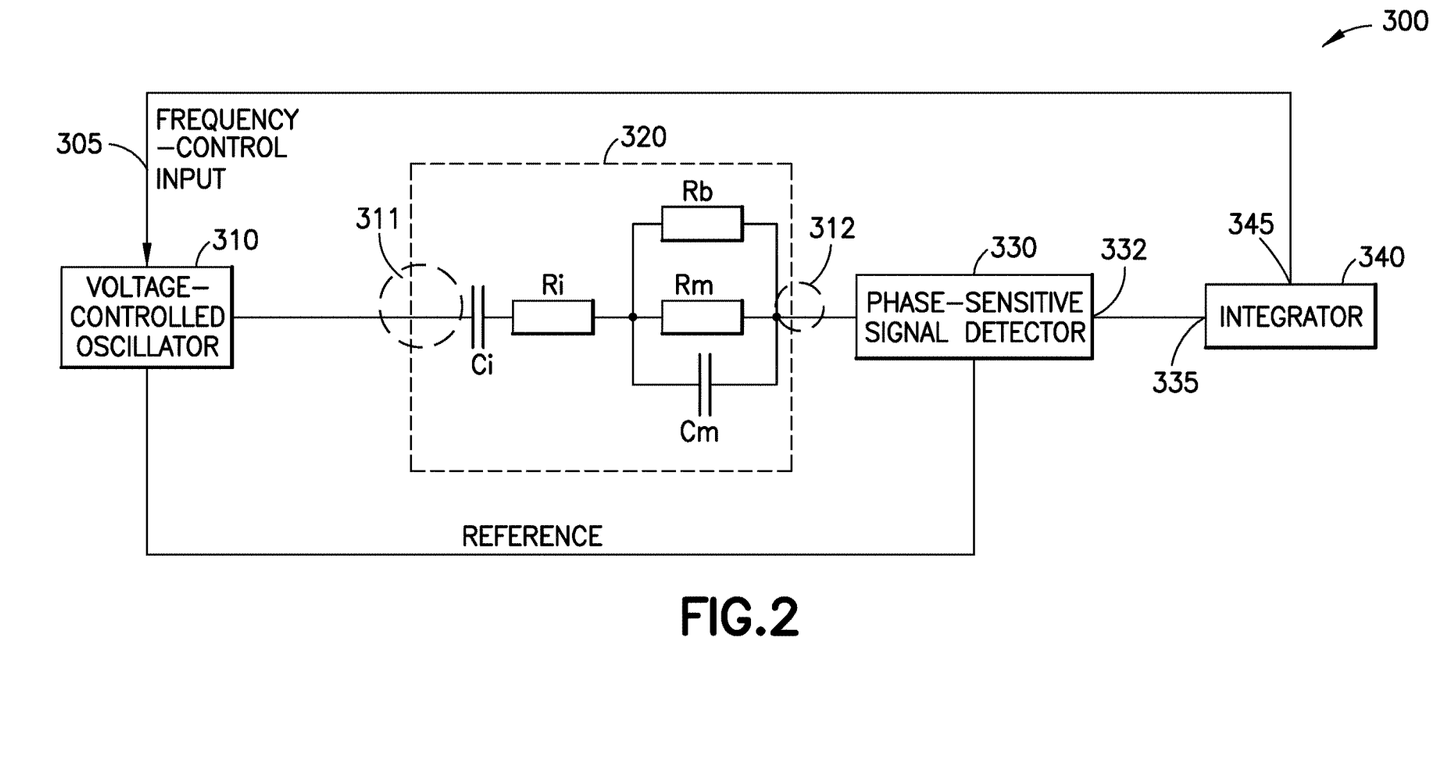
FIG. 2 illustrates another implementation of an apparatus for measuring the dielectric capacitance of a liquid sample to determine the presence or absence of microorganisms therein whereby the measuring frequency of the signal generator is automatically tuned to and kept at the zero-crossing frequency.

FIG. 2 illustrates an alternate implementation of an apparatus for measuring the dielectric capacitance and reactance of a liquid sample to determine changes in the ionic charge of the test environment using an automatic tuning of the measurement frequency. In this regard, the out-of-phase signal output 332 of a phase-sensitive signal detector 330 is connected to the input 335 of an electronic integrator 340. The output 345 of the integrator 340 is connected to the frequency-control input 305 of a voltage-controlled oscillator 310 that acts as the signal generator as in the apparatus shown in FIG. 1. Again, Ci represents the interface capacitance between the metal electrodes and the liquid; Ri represents the interface resistance between the metal electrodes and the liquid; Rb is the bulk resistance of the liquid; and Cm is the bulk capacitance. Additionally, bulk capacitance (Cb), as discussed in WO 2013/123189, which has been incorporated by reference, may be used to detect microbial growth.

In this embodiment, a sinusoidal electrical signal is generated by a voltage-controlled oscillator ("VCO") 310 and electrically coupled to an electrode 311 in contact with the sample. A second electrode 312, also in contact with the sample, is electrically connected to a phase-sensitive signal detector 330. As stated above, the out-of-phase output signal of the phase-sensitive signal detector is coupled to the integrator 340. Because the output of the integrator 340 is coupled to the frequency-control input of the VCO 310, the frequency of the VCO 310 is adjusted until the out-of-phase signal amplitude measured by the phase-sensitive signal detector is at zero. Over time, an increase in the tuned frequency at zero out-of-phase signal amplitude indicates microorganism growth within the sample.

In operation, the integrator 340 output voltage affects the frequency of the voltage-controlled oscillator. For example, if the starting frequency is below 60 kHz, the out-of-phase signal amplitude is positive. This leads to a positive output voltage at the integrator output 345 and, consequently, to an increase in the frequency of the voltage-controlled oscillator 310. The increase in frequency will continue until the zero-crossing frequency is reached (where the out-of-phase-signal amplitude is zero). At this moment, when the out-of-phase amplitude becomes zero, no further integration occurs. Thus, the frequency of the voltage-controlled oscillator is left at the zero-crossing frequency, which is 60.723 kHz according to this example. If the initial frequency is too high, the actual zero-crossing frequency would be automatically approached from the too high frequency. The presence of bacteria could be detected by recording the zero-crossing frequency over time and detecting an increase in frequency attributable to microbial growth.

The advantage of the apparatus illustrated in FIG. 2 is that a zero-crossing frequency can be determined with extremely high precision. Due to the fact that a "Zero Signal" is generated at the output of the phase-sensitive signal detector, any drift in the signal generator amplitude or in the internal gain of the phase-sensitive signal detector will not affect the automatically tuned zero-crossing frequency, which represents the system output information.

Figure 3:
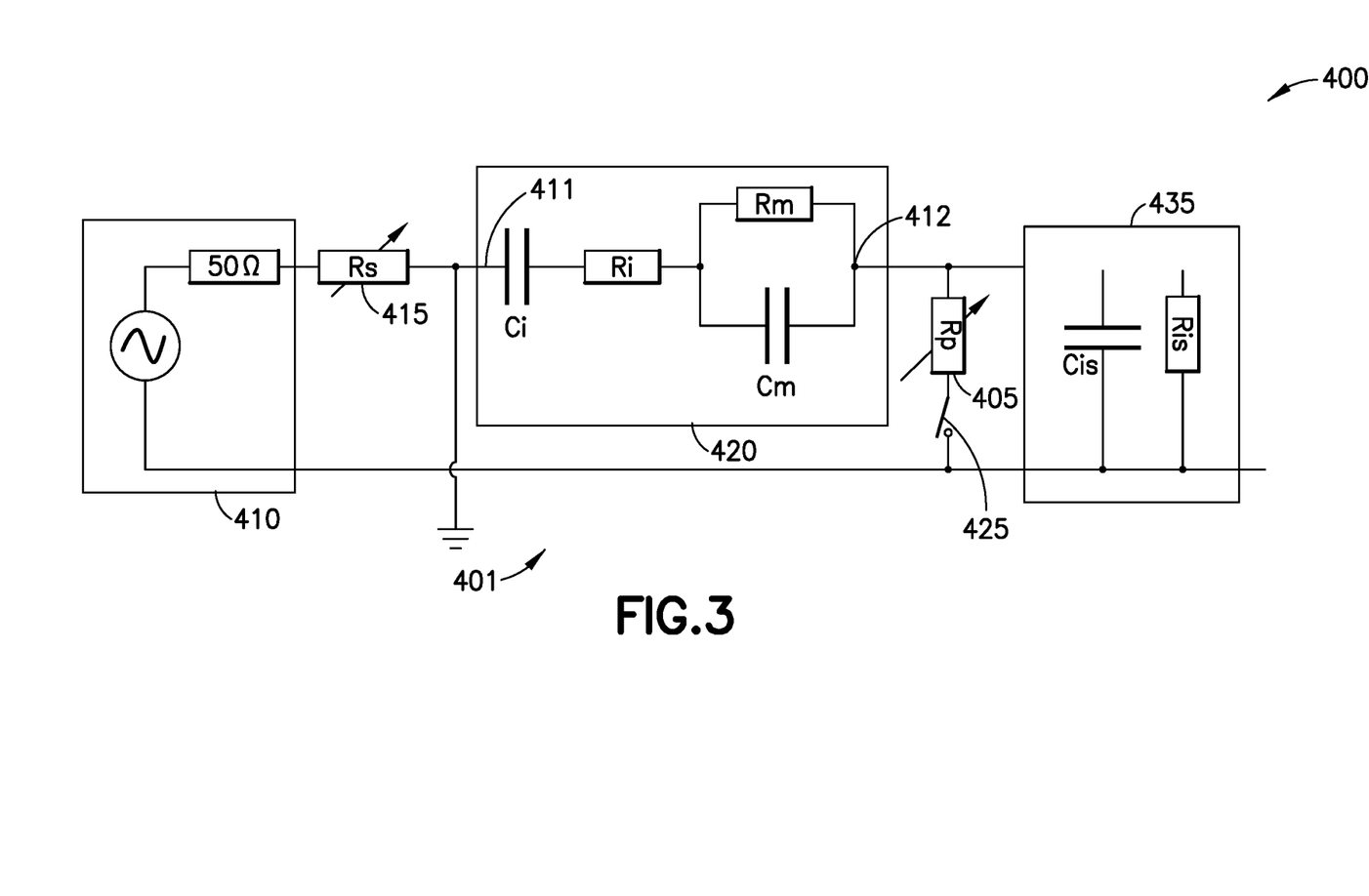
FIG. 3 illustrates an example of an apparatus for measuring the reactance of a liquid sample to determine the presence or absence of microorganisms therein.

Turning to FIG. 3, an implementation of a system 400 for measuring impedance using a bridge resistor (Rp)-capacitor tuning circuit 405 is shown. The system of FIG. 3 includes a output stage 410 of a lock-in amplifier with an internal signal generator, a variable series tunable element 415 (i.e. a variable potentiometer), a consumable 420 containing a liquid sample, a bridge resistor-capacitor tuning circuit (e.g., a second variable potentiometer 405 and a switch 425 wired in series), and an input stage 435 of the lock-in amplifier. In the illustrated embodiment, when the switch is open the system operates at a low frequency, and when the switch is closed the system operates at high frequency.

As described above, the lock-in amplifier with an internal signal generator has a typical internal resistance of 50Ω. Additionally, the lock-in amplifier input stage 435 has a typical capacitance (Cis) of 15 pF and a typical input resistance (Ris) of 10 MΩ. In this regard, the lock-in amplifier may generate the voltage and frequency applied to the liquid sample. Further, one of ordinary skill in the art would recognize that measuring devices, such as an LCR meter or a network analyzer, may be used without departing from the scope of the examples described herein.

The variable bridge tunable element (Rs) (e.g., a variable potentiometer) 405 functions like the source-matching resistor discussed above. Accordingly, the variable bridge tunable element (Rs) 405 may be tuned to a resistance (0-10, 000Ω) for a given consumable 420 (i.e., measuring chamber) and sample liquid, such that the frequency spectrum of the out-of-phase component of the measurement signal shows a zero-crossing feature that (i) is dependent on the value of Cm, and (ii) is positioned at a conveniently low frequency below 100 kHz. This allows for the use of standard lock-in amplifiers.

The consumable 420 is largely a matter of design choice. In this described embodiment, the consumable is a plastic bottle or similar plastic consumable (not shown) with two apertures on the side spaced apart between about 10 mm to about 40 mm. A metalized electrode (e.g., a brass cylinder piece electroplated with gold) is placed in each aperture and epoxy (e.g., glue) placed around the outside plastic/metal interface to fix the electrode in place. It is important to note that the epoxy is only found on the outer surface and does not penetrate into the inner area of the bottle containing the sample. That is, the epoxy does not contact the sample.

One of ordinary skill in the art would recognize that the consumable may have variety of geometries and adapter ports for sterile transfer of sample into and out of said consumable. In this regard, different consumables may be used based on the patient specimen types, volumes of samples to be tested, etc.

The metalized electrodes 411, 412 may be made of any standard (i.e., low-cost) metal (e.g., copper, brass, steel, etc.) that has a conformal coating (i.e., sub-nm to micron thickness) with a non-corroding metal (e.g., platinum, gold, silver) applied thereto. This conformal coating of a non-corroding metal is necessary to be compatible with high salt growth/media matrices (e.g. blood, urine, sputum). Examples of conformal coating techniques include electroplating, sputtering, and evaporation processes. Such processes are well known to one skilled in the art and not described in detail herein. One of ordinary skill in the art would select among convention conformal coating techniques to form the electrodes described herein.

The electrode configuration may be adapted to virtually any size, geometry, and material used in a consumable (i.e., test device). The electrodes (2 or more) may be configured into any consumable format that has been provided with appropriate sized features to receive the electrodes. In alternative embodiments, the consumable may be formed by blow molding the consumable around the electrodes. In other examples, the electrodes may extend into the consumable through the cap of the consumable. This design does not require molding or gluing the electrodes directly into the material of the consumable. In above-described embodiments, the electrodes may be configured to form a conduction path between the outside world and inner contents (i.e., liquid) of the consumable.

Examples of consumables include traditional vials, tube configurations, microfluidic cartridges, etc. Suitable consumables are well-known to one skilled in the art and are not described in detail herein.

Examples of suitable metals for the electrode, include, but are not limited to, silver, gold, zinc, iron, nickel, aluminum, etc. Furthermore, different metal coatings could be used for the electrodes. Additionally, the electrode spacing, trace wire configurations, and electrode dimensions are largely a matter of design choice. The electrode design depends on a variety of factors, such as the medium, the consumable, the sample, etc. One of ordinary skill in the art would recognize that a variety of configurations may be used based on the examples described herein.

In operation in those embodiments where the electrodes are positioned inside the consumable, the electrodes must be immersed within the sample liquid such that there is a conduction path between the electrodes. In other words, the same body of liquid that covers one electrode must also cover the other. Furthermore, the presence of non-biological objects within the bottle (e.g., epoxy, resin) must not cover the electrodes to an extent that may disturb the conductive path between electrodes resulting in highly variable and unreliable data.

The system is configured to receive the consumable (schematically illustrated in FIG. 3) such that it will be integrated electronically into the system 400. According to some embodiments, an asymmetric feature may be formed into the consumable such that the user can only insert the consumable into the instrument in one pre-determined orientation. This will ensure proper interconnection between the consumable "module" and the other components in the system.

Figure 4A:
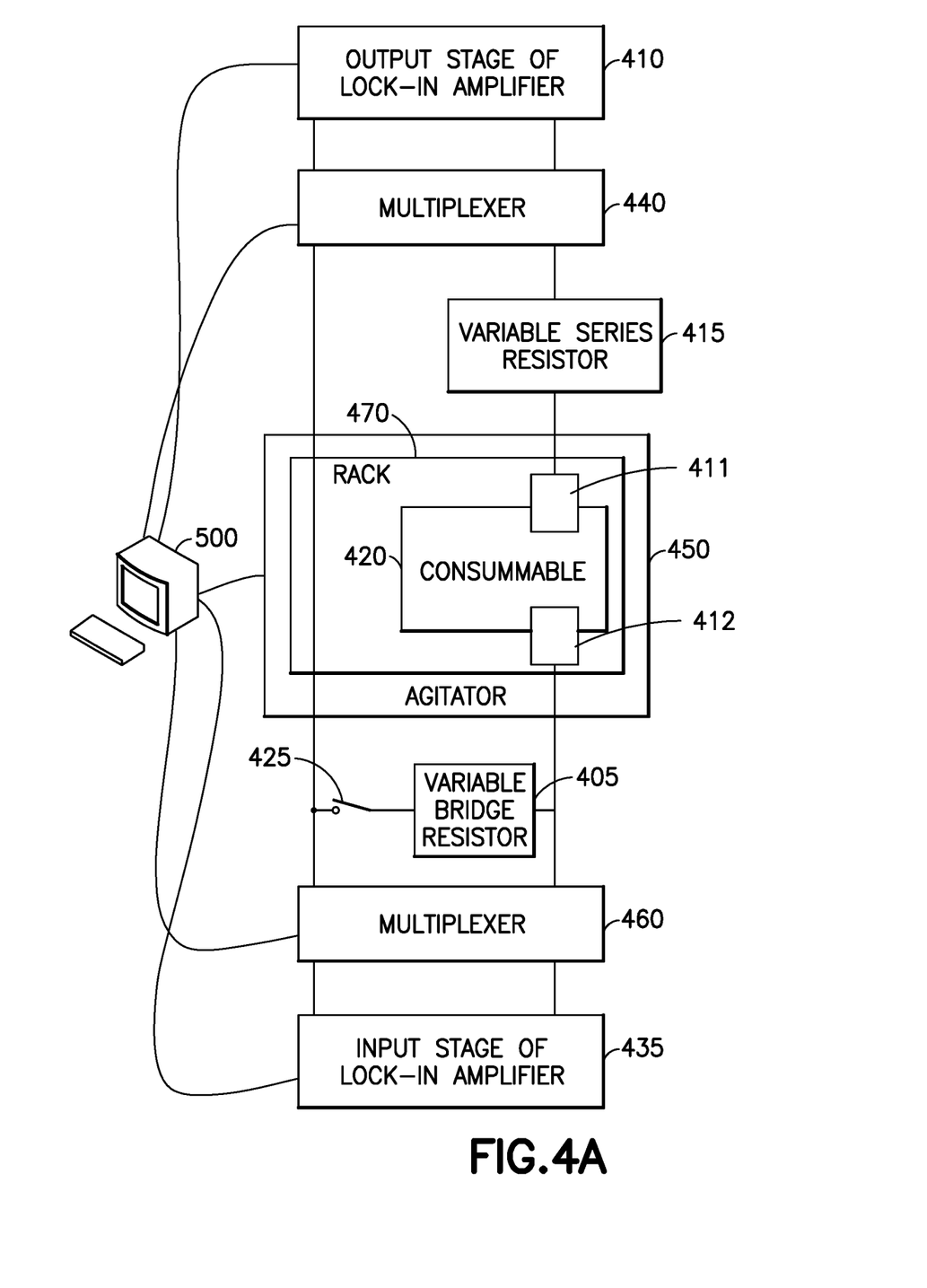
FIGS. 4A and 4B illustrate block diagrams of the apparatus for measuring the reactance of the liquid sample.
Figure 4B:
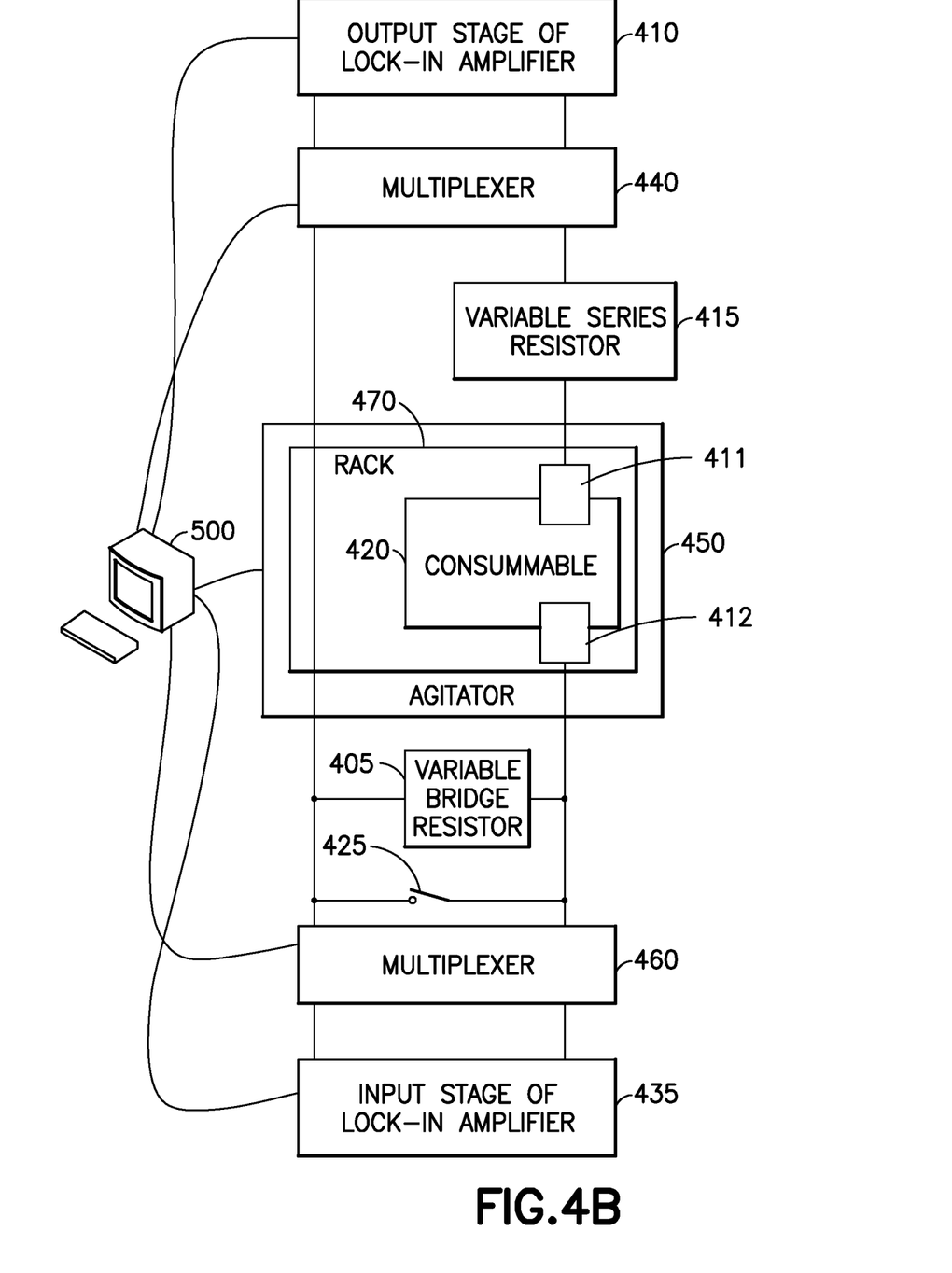

Turning to FIGS. 4A and 4B, various implementations of system 400 are shown for measuring impedance in multiple consumables. The system of FIGS. 4A and 4B include an output stage 410 of a lock-in amplifier, a multiplexer 440, a variable series resistor 415, a consumable 420 with a first electrode 411 and a second electrode 412, an agitator 450, a rack 470, a variable bridge resistor 405, a second multiplexer 460, an input stage 435 of the lock-in amplifier, and a computer 500. In FIG. 4A, the switch 425 is in series with the variable bridge resistor 405. Such relationship between the switch 425 and bridge resistor 405 is also illustrated in FIG. 3. FIG. 4B is an alternate configuration where switch 425 is parallel to variable bridge resistor 405.

According to this embodiment, the consumables 420 may be stored in a rack-based modular platform 470. Each rack 470 may include multiplexer elements that can address up to 20 consumables. Accordingly, there may be at least one dedicated digital signal processing (DSP) lock-in amplifier module per rack that will be responsible for signal acquisition. Therefore, the present invention contemplates an array of consumables and switches which will permit signal acquisition for each consumable in the array.

The multiplexer circuitry 440 and 460 may allow a computer (e.g. 500), single detection board or instrument to scan a plurality of consumables or sub-components of a single consumable. In those embodiments where one consumable has multiple chambers with sample in each of the multiple chambers, the multiplexers act to "switch" the connection (1+ input and 1+ output) of the detection instrument/circuit to a single consumable or sub-component of a consumable. The multiplexer circuitry would allow for relatively few hardware components to monitor a plurality of consumables. The multiplexer circuitry may have a number of operating variations, depending upon the extent of multiplexing and consumable configurations.

In operation, measurements of the consumables may be done serially. That is, each consumable in the array may be scanned one at a time. The scan time per consumable may be on the order of tens of seconds. Therefore, each rack (if completely full) will take roughly 2-3 minutes to scan. The computing device 500 may repeat the scanning action every 10-minutes. When the array is not being scanned, it may agitate the consumables using the agitator 450 to fully mix and aerate the liquid. Agitation may be performed through vertical displacement, orbital shaking, or through the use of stir-bars within the consumable. The agitation mechanism (if required) may have a variety of configurations including horizontal shaking mechanisms to maximize sample mixing. One of ordinary skill in the art would recognize that different examples of agitators may be used from the examples described herein and are therefore not discussed in greater detail.

The variable bridge resistor 405 (e.g., bridge resistor-capacitor tuning circuit) may be an external tuning circuit that physically connects the consumable 420 to the detection instrument (i.e. the input stage 435 of the lock-in amplifier). The variable bridge resistor 405 may contain a series of parallel variable resistors (digital potentiometers) that allow for "on-the-fly frequency tuning and calibration" of the frequency sensitivity. In this regard, the frequency of the signal from the consumable may be tuned to between about 1 kHz and about 200 MHz. The tuning parameters (i.e., frequency range selected and peak-to-peak voltage) may be determined by the total volume of the consumable, the metallization of the electrode (e.g. Au, Ag, or Pt), the type of liquid contained, etc. By tuning the consumable signal at both low and high frequencies, the system is able to detect metabolic by-products at low frequencies and organism biomass at higher frequencies independently.

According to some implementations, a switch 425 may be wired in series with the series of variable bridge resistor 405 as shown in FIG. 4A. In alternative examples, the switch 425 may be wired in parallel with the variable bridge resistor 405 as shown in FIG. 4B. When the switch is open, the system may operate at a low frequency (i.e., 1 to 20 kHz). As noted above, this will enable detection of changes in the make-up of the consumable. When the switch is closed, the system may operate at higher frequencies (i.e., >>20 kHz) by providing feedback to the signal generator. As previously discussed, by operating at higher frequencies, the system becomes sensitive to both changes in ionic composition of the liquid and the organism mass itself. By having the ability to tune the frequency to test at both high and low frequencies, the system may yield faster time-to-detections (TTDs) with lower volumes of sample.

The input stage of the lock-in amplifier 435 is a specialized piece of equipment that can extract a signal with a known frequency from within an extremely noisy environment. Furthermore, a lock-in amplifier may decompose a signal into principle subcomponents that are of particular interest. For example, a component of the total impedance, specifically the "out-of-phase" reactance component may be used according to:

$$Z = \text{Resistance} + j*\text{Reactance}$$

$$\text{Total Impedance } |Z| = \sqrt{\text{Resistance}^2 + \text{Reactance}^2}.$$

In another example, the capacitive components (i.e., interface capacitance and cellular capacitance) contribute towards the total reactance subcomponent. Accordingly, using subcomponents of the signals may 1) allow for continuous monitoring of each consumable or subcomponent of a consumable at specified intervals (e.g. about 10 minutes) for several days (e.g. 5 day protocol) and 2) detect changes in the composition of charged molecules and number of biological cells or components of the sample.

In this regard, a data analysis may be performed once the signals are input into the input stage 435 of the lock-in amplifier. According to some embodiments, the data analysis is performed in two steps to determine microbial growth. First, raw spectral data (i.e., detected reactance signal vs. frequency) is analyzed (e.g. slope, area under the curve, x-intercept, y-intercept, etc.) at each point in time to arrive at a single data point. Second, after a plurality of data points are obtained per consumable or subcomponent of a consumable, a generalized algorithm is applied to determine at which point a statistically significant deviation from known control values indicates the presence of an organism. Due to the enhanced sensitivity to microbial growth, the examples described herein provide faster detection times of microbial growth.

In alternative embodiments, a single extracted data value from the raw "reactance" data may be used to determine the presence or absence of microbial growth. In this regard, the extracted data may use mathematical functions to determine intercepts or areas under a curve. The results of these mathematical functions may be compared to threshold values. Thus, cumulative changes above threshold values may be used to differentiate between organism-containing consumables. Accordingly, the frequency spectrum of the out-of-phase component of the measurement signal shows a zero-crossing feature that (i) is dependent on the value of Cm, and (ii) is set at a conveniently low frequency. In certain embodiments that frequency is set at a value at or below about 100 kHz. This allows for the use of standard measuring devices, such as the lock-in amplifiers described herein, LCR meters, and/or network analyzers.

The above-described embodiments improve time-to-detection (TTD) by 5-70% as compared to standard optical methods. As described below, data shows that detection of a number of organisms can occur with a faster TTD when examined under low frequency tuning as compared to traditional optical methods. Furthermore, the data indicates that detection sensitivity may be further enhanced using high frequency tuning, thereby resulting in an even faster TTD.

Figure 5:
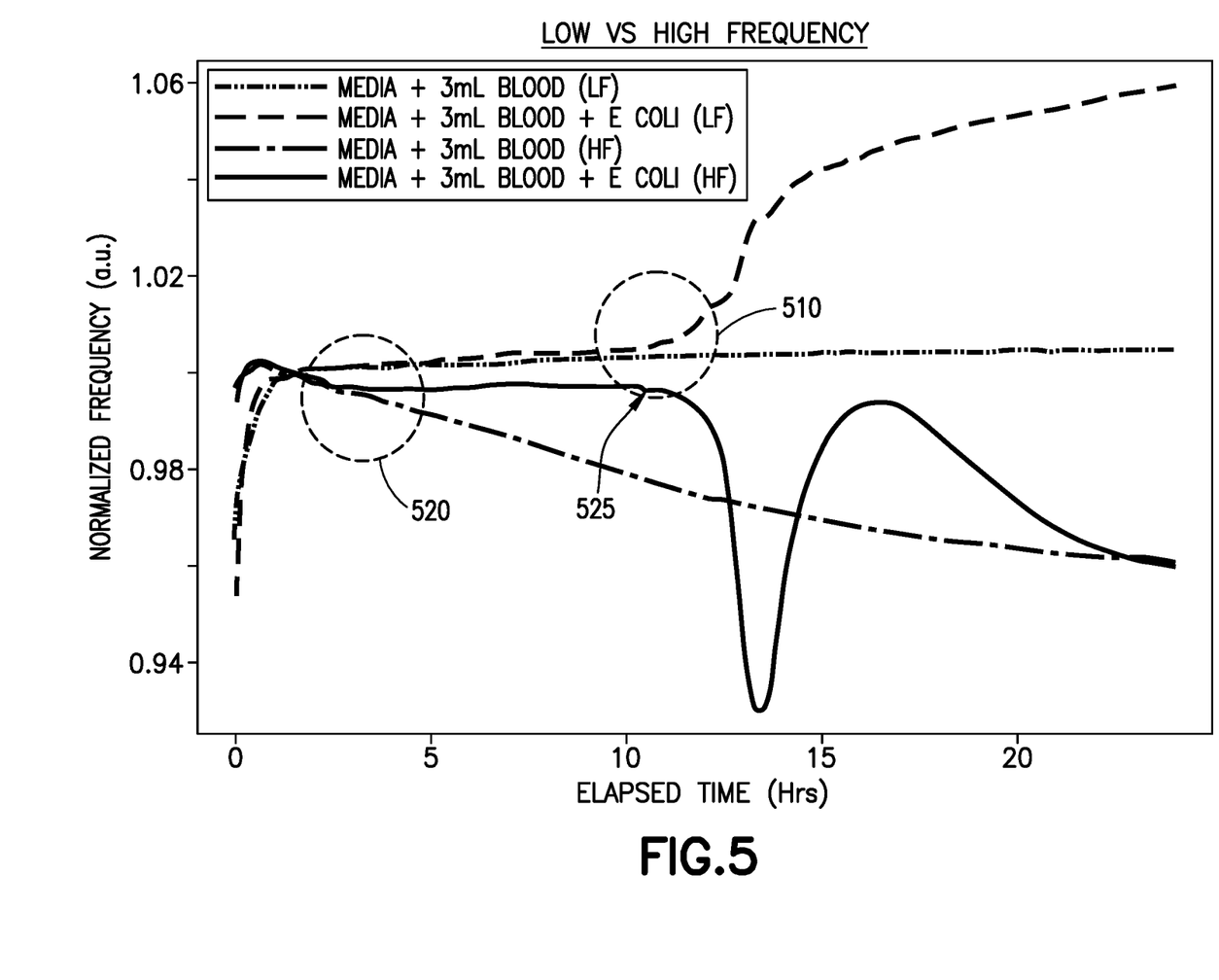
FIG. 5 illustrates a line graph showing the time to detection of *E. coli* at different frequencies.

In this regard, as illustrated in FIG. 5, an experiment was conducted with a smaller polycarbonate tube that contained: 10 mL of BACTEC standard aerobic medium, 3 mL of bagged blood, 17 CFU (colony forming units) of E. coli organisms (A25922), and Au-plated metal electrodes (brass body) extending into the interior of the consumable and immersed in the medium/sample mixture. The electrodes in the consumable were interconnected with the other components of the lock-in amplifier. The bridge resistor setup for the instrument was set to 187 Ohms, resulting in a spectral sensitivity in the 40 to 80 kHz band.

Figure 6:
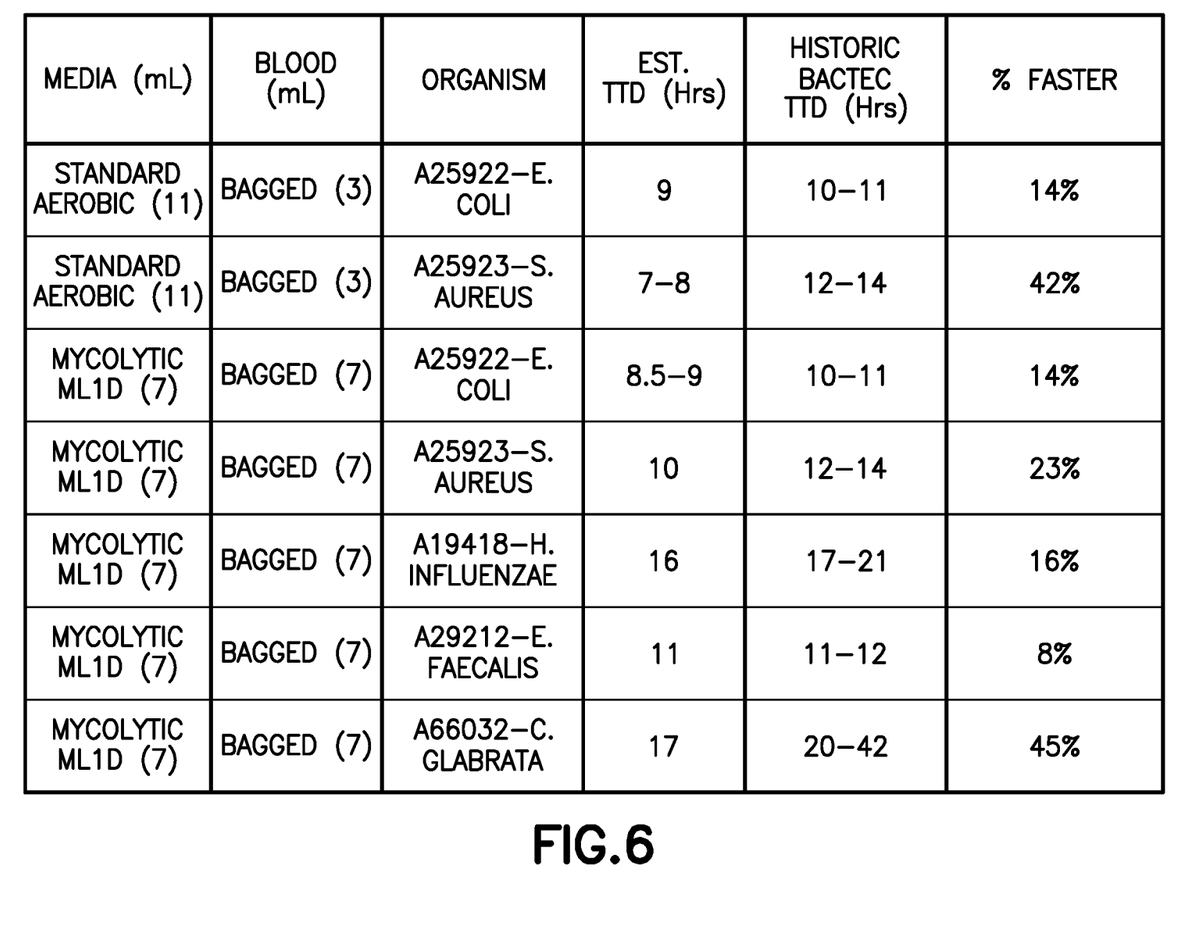
FIG. 6 illustrates reduced time-to-detection times realized by the embodiments described herein.

When compared to controls (no organism) tube, which were scanned in parallel, TTDs improved significantly for most organisms and media as illustrated in FIG. 6. This may indicate organism sensitivity on the order of $10^4$-$10^5$ CFU, which is at least 2 to 4 orders of magnitude more sensitive than current optical measuring systems, which detect organism at approximately $10^9$ CFU. These results represent a 70% reduction in time to detection as discussed in greater detail below with respect to FIG. 5 Detection at these levels has never been reported and was completely unexpected. For illustration, the frequency changes over time are shown for E. coli (vs. control). At low frequency, TTD was approximately 10 hours, which is up to 5-10% faster. At high frequency, the TTD was improved to approximately 4 hours, which is almost 70% faster.

Referring again to FIG. 6, the above-described experiment, the results of which are illustrated in FIG. 5, was repeated for the variety of samples reported in FIG. 6. For example, with 3 mL of bagged blood and 17 CFU of S. aureus (A25923) growth was detected in 7-8 hours. In contrast to standard optical detection techniques which detect colony growth in approximately 12-14 hours, this represented a 42% reduction in time-to-detection.

FIG. 6 illustrates results of performing the experiment with 7 mL of bagged blood and 17 CFU of E. coli organisms (A25922); 7 mL of bagged blood and 17 CFU of S. aureus (A25923); 7 mL of bagged blood and 17 CFU of H. influenzae (A19418); 7 mL of bagged blood and 17 CFU of H. faecalis (A29212); and 7 mL of bagged blood and 17 CFU of C. glabrata (A66032).

Accordingly, in 7 mLs of mycolytic media the E. coli growth was detected in approximately 8.5 to 9 hours, which is an improvement in TTD when compared to standard optical detection techniques for detecting the growth of E. coli in mycolytic media (10-11 hours). The S. aureus growth in mycolytic media was detected in about 10 hours which represented a 23% improvement over standard optical detection techniques. H. influenzae colony growth in mycolytic media was detected in approximately 16 hours. This represented a 16% improvement over the TTD for H. influenzae (16 hours) using standard optical detection techniques. For H. faecalis colonies in mycolytic media, the TTD was 11 hours, representing an 8% improvement over a TTD of 11-12 hours using standard optical detection techniques. The TTD for C. glabrata colonies in mycolytic media was detected in approximately 17 hours, which represented a 45% improvement in TTD for C. glabrata (20-42 hours) using standard optical detection techniques. Improvement in TTD for this sample in standard aerobic media over standard optical techniques is also reported in FIGS. 5 and 6.

Figure 7:
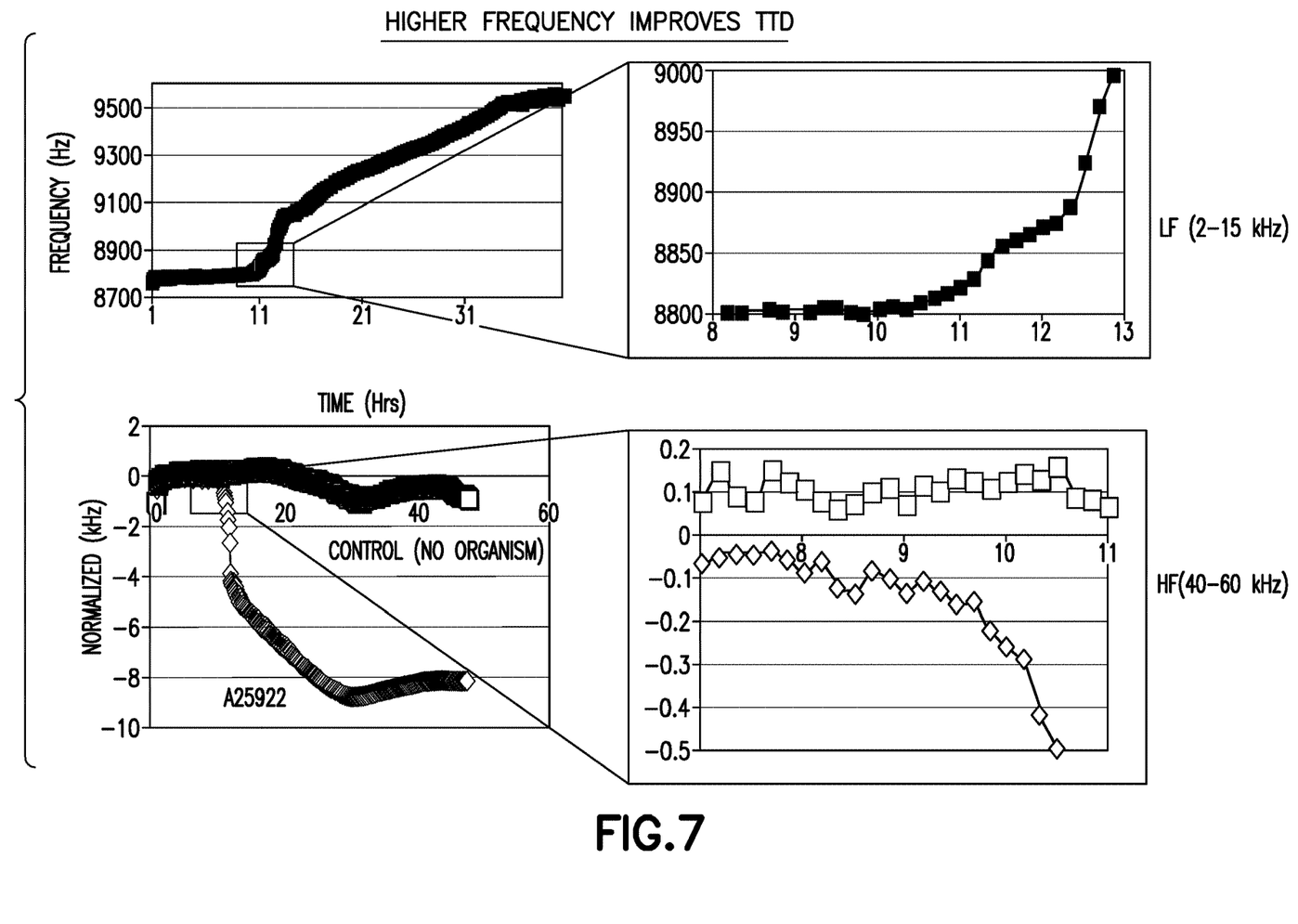
FIG. 7 shows experimental results that time-to-detection may be improved using higher frequencies.

FIG. 7 illustrates that the improved time to detection achieved for the smaller volumes described above is also achieved for larger volumes of sample/media. Specifically, 40 ml of standard BACTEC media and 10 ml of blood were combined in a BACTEC bottle. The sample was spotted with 50-60 CFU E. coli. At low frequency, using the apparatus and method described herein, TTD was 10.5-11 hours, which is up to 5% faster. At high frequency, the TTD was improved to 9.5-10 hours, which is up to 14% faster.

FIG. 5 illustrates the time-to-detection of E. coli at different frequencies. All consumables were prepared the same way and the only difference was the presence or absence of organisms and the electrical parameters of the external circuit. In this regard, the experiment was performed with four 16 mL consumables, each prepared with 10 mL of standard aerobic medium and 3 mL of blood. Two of the consumables also had 17 colony forming units of the *E. coli* added (one for low frequency mode and one for high frequency mode). The electrodes of the consumable were 30 mm gold electrodes. During the experiment, a 500 mV peak-to-peak voltage was applied to the consumable and the consumable was agitated via shaking at a rate of 120 rotations per minute.

In the low frequency mode (e.g. 1-10 kHz), there was no deviation in the applied signal in the consumable with media and blood. In comparison, a deviation in frequency was detected for the consumable with *E. coli* added in the low frequency mode at around 10 hours, as depicted in FIG. 5 at signal deviation point 510. This represents a 5-10% improvement in time to detection over standard optical detection techniques. The historic BACTEC TTD for *E. coli* is approximately 11 hours.

In the high frequency mode (e.g., 40-80 kHz), the variable bridge resistor (e.g., 405 in FIGS. 4A and 4B) was tuned to 500Ω. Accordingly, a deviation from the applied signal was detected in the consumable with *E. coli* at around the four (4) hour mark, as depicted in FIG. 5 at signal deviation point 520. This represents a 70% improvement in time to detection over standard optical detection techniques. As with the earlier *E. coli* experiment, detection at these levels in this timeframe has never been reported and was completely unexpected. While the inventor does not wish to be held to a particular theory, this early detection feature at signal deviation point 520 is believed to be primarily attributable to cellular capacitance, or charge associated with the membrane potential of the microbial cells. As the cells continue to replicate and produce metabolic by-products, the ionic concentration of the media reaches a tipping point at which a second feature occurs, as depicted in FIG. 5 at signal deviation point 525. Both signatures represent a unique feature set with potential of a preliminary identification of the growing organism. Thus, the current application describes enhancing detection sensitivity by using both high and low frequency detection to yield a lower time-to-detection.

Figure 8:
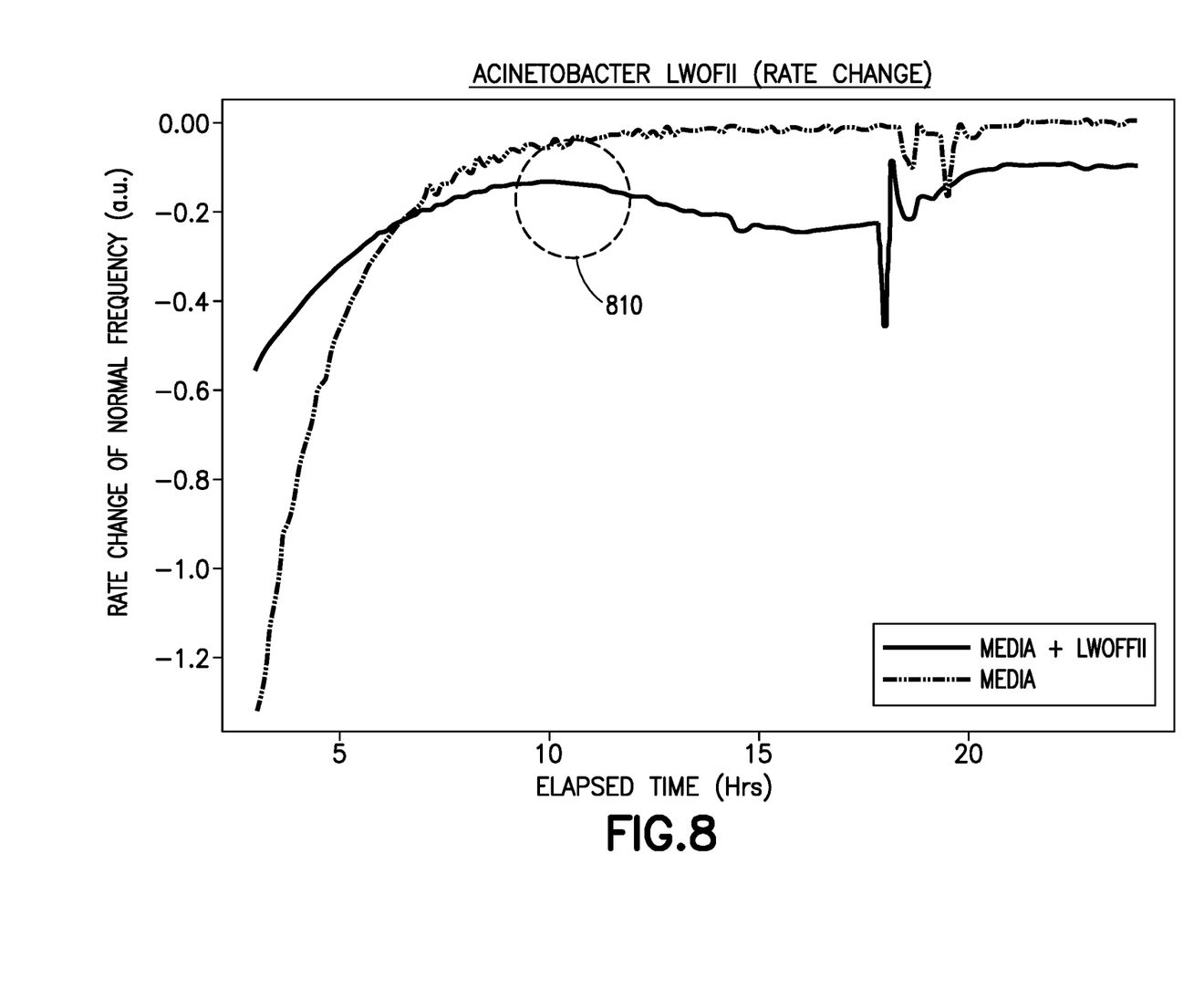
FIG. 8 illustrates a line graph showing the time to detection for *A. lwoffii* at high frequencies.

FIG. 8 shows the time to detection for *A. lwoffii* in a high frequency mode by measuring the rate of change as a function of time. The variable bridge resistor (e.g., 405 in FIGS. 4A and 4B) was tuned to 200Ω. The frequency band was 50-60 kHz. Two 1 mL consumables (e.g. a control and one with sample) were prepared with 0.9 mL of standard aerobic media and 0 mL of blood. According to this experiment, 28 colony forming units of *A. lwoffii* were added to one of the consumables. The consumables had two 15 mm electrodes. During the experiment, a 250 mV peak-to-peak voltage was applied to the consumable and the consumable was agitated via shaking at a rate of 100 rotations per minute. When a high frequency was applied, a rate change of the normal frequency was detected around 11 hours, as depicted in FIG. 8 at signal deviation point 810. This represented a 50% reduction in traditional optical detection systems. The historic BACTEC TTD for *A. lwoffii* is approximately 20 hours.

Figure 9:
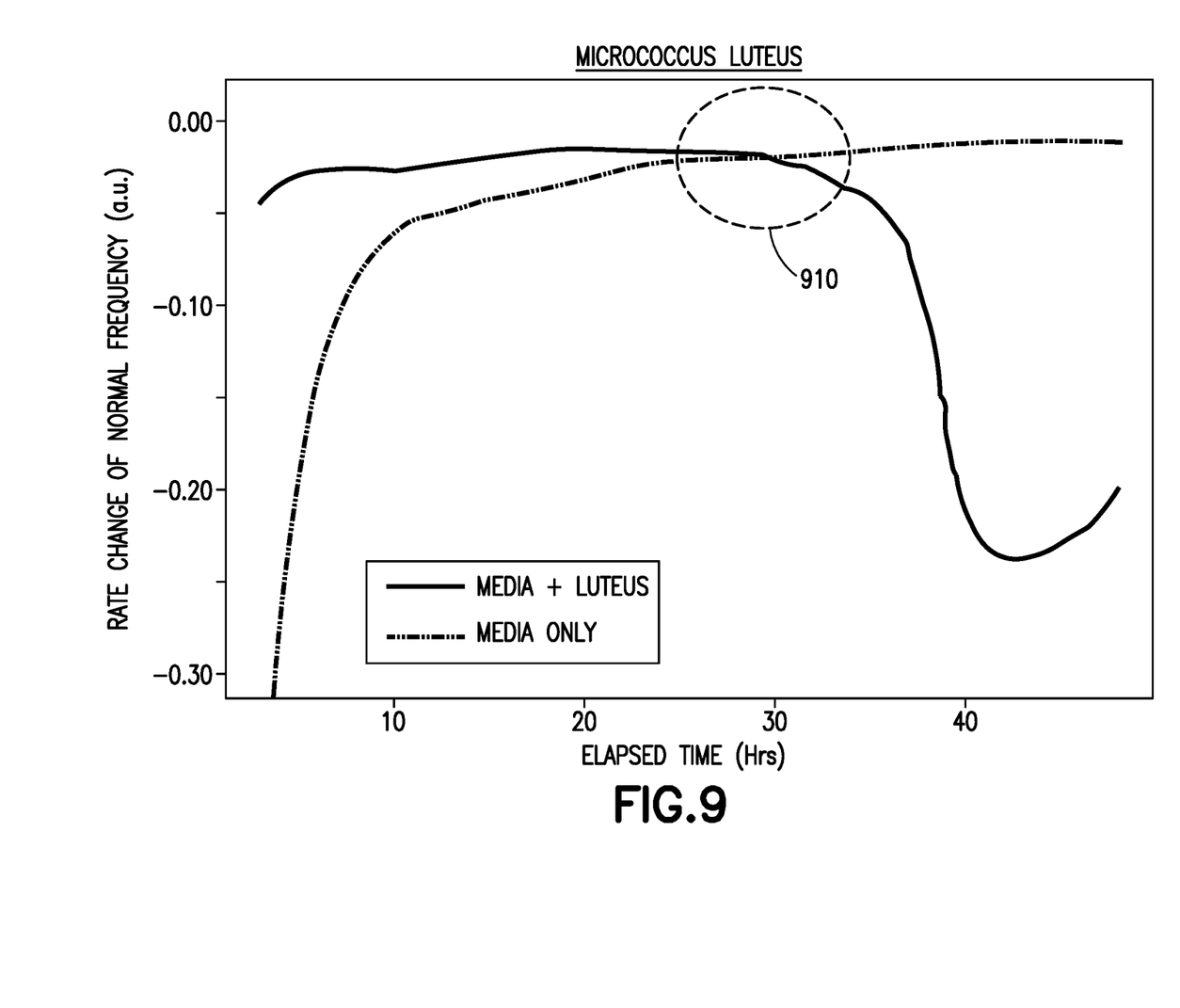
FIG. 9 illustrates a line graph showing the time to detection for *M. luteus* at high frequencies.

FIG. 9 represents the experimental results of detecting *M. luteus* in a high frequency mode. The variable bridge resistor (e.g., 405 in FIGS. 4A and 4B) was tuned to 200Ω. The frequency band was 60-70 kHz. Two 1 mL consumables (e.g. a control and one with sample) were prepared with 0.9 mL of standard aerobic media and 0 mL of blood. One of the consumables had 21 colony forming units of *M. luteus* added thereto. The consumables had two 15 mm electrodes. During the experiment, a 250 mV peak-to-peak voltage was applied to the consumable and the consumable was agitated via shaking at a rate of 100 rotations per minute. As shown in FIG. 9 at signal deviation point 910, a rate change of the normal frequency was detected around 28-30 hours, which is a 30% reduction over traditional optical detection systems. The historic BACTEC TTD for *M. luteus* is approximately 42 hours.

The detection times described above have never been reported and were completely unexpected. Thus, the current application describes enhancing detection sensitivity by using both high and low frequencies to yield lower times-to-detection for microbial growth.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An impedance-based method for detecting microbial growth, the method comprising:
   providing a vessel with at least two electrodes disposed therein;
   introducing a sample to be monitored for microbial growth in the vessel, the vessel having a volume of at least 10 mL, wherein the electrodes are immersed in the sample;
   measuring total impedance of the sample to determine a total ionic composition of the sample over time;
   from the measurement, determining an imaginary reactance component of the total impedance over time;
   determining changes in the imaginary reactance component over time; and
   from the determination of the changes in the imaginary reactance component over time, determining whether microorganism growth has occurred.

2. The impedance-based method of claim 1, further comprising tuning a frequency sensitivity of a system to the determined imaginary reactance component.

3. The impedance-based method of claim 2, wherein the tuning is by adjusting a resistance of one or more resistors in parallel with a capacitive input stage of a lock-in amplifier detector.

4. The impedance-based method of claim 2, wherein the tuning is by a bridge resistor-capacitor tuning circuit.

5. The impedance-based method of claim 1, wherein the total impedance is measured at a high frequency of about 40 kHz to about 80 kHz.

6. The impedance-based method of claim 1, wherein the total impedance is measured at a low frequency of about 1 kHz to about 10 kHz.

7. An impedance-based method for detecting microbial growth, the method comprising:
   providing a vessel with at least two electrodes disposed therein;
   introducing a sample to be monitored for microbial growth in the vessel, wherein the electrodes are immersed in the sample;
   measuring total impedance of the sample to determine a total ionic composition of the sample over time;
   from the measurement, determining an imaginary reactance component of the total impedance over time;
   determining changes in a zero-crossing frequency for the imaginary reactance component over time; and from the determination of the changes in the zero-crossing frequency for the imaginary reactance component over time, determining whether microorganism growth has occurred.

8. The impedance-based method of claim 7, wherein microorganism growth is determined to have occurred when the zero-crossing frequency for the imaginary reactance component increases over time.

9. The impedance-based method of claim 7, further comprising:
   providing a signal processing electronic circuit electrically coupled to the electrodes, the signal processing electronic circuit configured to detect an imaginary reactance component of total impedance; and
   tuning a frequency sensitivity of the signal processing electronic circuit to measure imaginary reactance.

10. The impedance-based method of claim 9, wherein the tuning is by adjusting a resistance of one or more resistors in parallel with a capacitive input stage of a lock-in amplifier detector.

11. The impedance-based method of claim 9, wherein the tuning is by a bridge resistor-capacitor tuning circuit.

12. The impedance-based method of claim 7, wherein the total impedance is measured at a high frequency of about 40 kHz to about 80 kHz.

13. The impedance-based method of claim 7, wherein the total impedance is measured at a low frequency of about 1 kHz to about 10 kHz.

14. The impedance-based method of claim 7, wherein the vessel has a volume of at least 10 mL.

* * * * *